(12) United States Patent
Marquais-Bienewald et al.

(10) Patent No.: US 8,992,633 B2
(45) Date of Patent: Mar. 31, 2015

(54) DISULFIDE DYES

(75) Inventors: Sophie Marquais-Bienewald, Hegenheim (FR); Christian Cremer, Lorrach (DE); Beate Frohling, Neustadt (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/114,783

(22) PCT Filed: May 2, 2012

(86) PCT No.: PCT/IB2012/052178
§ 371 (c)(1),
(2), (4) Date: Oct. 30, 2013

(87) PCT Pub. No.: WO2012/150549
PCT Pub. Date: Nov. 8, 2012

(65) Prior Publication Data
US 2014/0157529 A1     Jun. 12, 2014

Related U.S. Application Data

(60) Provisional application No. 61/481,760, filed on May 3, 2011.

(30) Foreign Application Priority Data

May 3, 2011   (EP) .................................. 11164596

(51) Int. Cl.
| | | |
|---|---|---|
| *A61Q 5/10* | (2006.01) | |
| *C09B 33/00* | (2006.01) | |
| *A61K 8/49* | (2006.01) | |
| *C09B 26/04* | (2006.01) | |
| *C09B 29/08* | (2006.01) | |
| *C09B 43/18* | (2006.01) | |
| *C09B 43/44* | (2006.01) | |
| *C09B 44/10* | (2006.01) | |
| *C09B 49/00* | (2006.01) | |
| *A61Q 5/04* | (2006.01) | |
| *A61Q 5/06* | (2006.01) | |
| *C09D 15/00* | (2006.01) | |
| *C09B 29/36* | (2006.01) | |

(52) U.S. Cl.
CPC ................ *A61K 8/4986* (2013.01); *A61Q 5/10* (2013.01); *C09B 26/04* (2013.01); *C09B 29/081* (2013.01); *C09B 43/18* (2013.01); *C09B 43/44* (2013.01); *C09B 44/10* (2013.01); *C09B 49/00* (2013.01); *A61K 8/49* (2013.01); *A61Q 5/04* (2013.01); *A61Q 5/065* (2013.01); *A61K 2800/884* (2013.01); *C09D 15/00* (2013.01); *C09B 29/3691* (2013.01)
USPC ................ 8/405; 8/409; 8/412; 8/426; 8/432; 8/435; 8/466; 8/565; 8/567; 8/568; 132/202; 132/208; 534/759

(58) Field of Classification Search
USPC ............. 8/405, 409, 412, 426, 432, 435, 466, 8/565, 567, 568; 132/202, 208; 534/759
See application file for complete search history.

(56) References Cited

U.S. PATENT DOCUMENTS 7,488,354 B2 * 2/2009 Daubress et al. ................. 8/405
8,641,783 B2   2/2014 Marquais-Bienewald et al.

FOREIGN PATENT DOCUMENTS

| CN | 1853605 A | 11/2006 |
|---|---|---|
| CN | 1997340 A | 7/2007 |
| WO | 95/01772 A1 | 1/1995 |
| WO | 2011/054966 A2 | 5/2011 |

OTHER PUBLICATIONS

STIC Search Report dated Mar. 27, 2014.*
International Search Report Sep. 20, 2012.
Translation of CN 1997340 Jul. 11, 2007.
Translation of CN 1853605 Nov. 1, 2006.
Asquith et al., Communications—The Reactions of Disulphide Dyes for the Covalent Coloration of Keratin, JSDC, pp. 168-172 (May 1973).

* cited by examiner

*Primary Examiner* — Eisa Elhilo
(74) *Attorney, Agent, or Firm* — Shruti Costales

(57) ABSTRACT

Disclosed are compounds of formula (1) or formula (2). The compounds are useful for the dyeing of organic materials, such as keratin fibers, wool, leather, silk, cellulose or polyamides, especially keratin-containing fibers, cotton or nylon, and preferably hair, more preferably human hair. (1) (2).

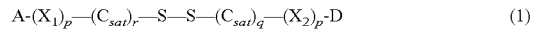

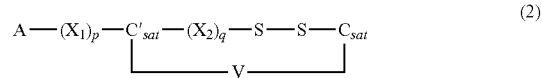

21 Claims, No Drawings

DISULFIDE DYES

The present invention relates to novel disulfide dyes, compositions thereof, to processes for their preparation and to their use for the dyeing of organic materials, such as keratin fibers, wool, leather, silk, cellulose or polyamides, especially keratin-containing fibers, cotton or nylon, and preferably hair, more preferably human hair.

It is known, for example, from WO 95/01772 that cationic dyes can be used to dye organic material, for example keratin, silk, cellulose or cellulose derivatives, and also synthetic fibers, for example polyamides. Cationic dyes exhibit very brilliant shades. A disadvantage is their unsatisfactory fastness to washing.

R. S. Asquith, P. Carthew and T. T. Francis describe in JSDC from May 1973, pages 168-172 that ortho-azo disulfide dyes do not lead to covalent bonding with keratin fiber of wool, and that para-azo disulfide dyes underwent only at high concentration some covalent bindings with wool.

The actual technical problem of the present invention was to provide dyes that are distinguished by deep dying having good fastness properties with respect to washing, light, shampooing and rubbing.

Accordingly, the present invention relates to compounds of formula

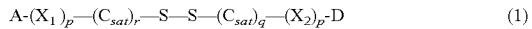

$$A\text{-}(X_1)_p\text{—}(C_{sat})_r\text{—}S\text{—}S\text{—}(C_{sat})_q\text{—}(X_2)_p\text{-}D \quad (1)$$

or formula

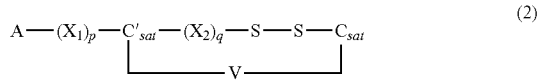

$$A\text{—}(X_1)_p\text{—}C'_{sat}\text{—}(X_2)_q\text{—}S\text{—}S\text{—}C_{sat} \quad (2)$$
$$\underbrace{\hspace{3cm}}_{V}$$

wherein

A is selected from a residue of a cationic dye;

$X_1$ and $X_2$, independently from each other are selected from saturated or unsaturated $C_1$-$C_{30}$hydrocarbon chains, optionally interrupted by at least one bivalent group chosen from —N($R_1$)—; $N^+(R_1)(R_2)$—; —O—; —S—; —CO—; —$SO_2$—; and/or optionally interrupted by an optionally substituted, saturated or unsaturated, fused or non-fused, aromatic or nonaromatic (hetero)cyclic radical optionally comprising at least one identical or different heteroatom;

V is $C_1$-$C_3$alkylene, optionally substituted by hydroxy;

D is a radical chosen from —N(CO)—$R_3$;

$C_{sat}$ and $C'_{sat}$ independently from each other are optionally substituted, optionally cyclic, linear or branched $C_1$-$C_{18}$alkylene chains;

$R_1$ and $R_2$, independently from each other are chosen from hydrogen; $C_1$-$C_4$alkyl; hydroxyalkyl; or aminoalkyl;

$R_3$ is $C_1$-$C_4$alkyl; and p, q and r independently from each other are 0; or 1.

Preferred are compounds of formula (1) or (2), wherein A is a radical of formula (1a) W—N=N—Ar—; (1b) Ar—N=N—W—; and (1c) Ar—N($R_4$)—N=CH—W— wherein

W is a fused or non-fused, aromatic or nonaromatic heterocycle comprising a quaternary ammonium;

Ar is chosen from $C_5$ or $C_6$aryl radicals and aromatic bicycles of the naphthyl type, which are optionally substituted with at least one halogen atom, at least one alkyl group, at least one hydroxyl group; at least one alkoxy group, at least one hydroxyalkyl group or at least one amino group or (di)alkylamino group; and $R_4$ is hydrogen; or $C_1$-$C_4$alkyl.

Preferably the residue of an organic dye is selected from azo, azomethin, hydrazomethin, merocyanine, methin and styryl dyes, and more preferred from azo, azomethin dye and hydrazomethin dyes;

Suitable nitroaryl dyes of the present invention are for example selected from the following compounds:

4-amino-1-nitrobenzene, 2-amino-6-chloro-4-nitrophenol, 2-amino-3-nitrophenol, 2-amino-1-nitrobenzene, 1,4-diamino-2-nitrobenzene, 4-acetylamino-1-amino-2-nitrobenzene, 1,2-diamino-4-nitrobenzene, 1-amino-2-methyl-6-nitrobenzene, 3-amino-6-methylamino-2-nitropyridine (Azarot), pikraminacid, 4-amino-3-nitrophenol, 4-amino-2-nitrophenol, 6-nitro-o-toluidine, 1, 4-bis-(2-hydroxyethyl) amino-2-nitrobenzene, 1-(2-hydroxyethyl) amino-2-nitro-benzene (HC Yellow No. 2), 1-(2-hydroxyethyl) amino-2-(2-hydroxyethyloxy-4-nitro-benzene (HC Yellow No. ), 1-amino-2-(2-hydroxyethyl) amino-5-nitrobenzene (HC Yellow No. 5), 1-(2, 3-dihydroxypropyl) amino-4-trifluormethyl-2-nitro-benzene (HC Yellow No. 6 ), 1-(2-hydroxyethyl)amino-4-chlor-2-nitro-benzene (HC Yellow No. 12), 1-amino-2-nitro-4-[bis(2-hydroxyethyl)]amino-benzene (HC Red No. 13), 4-chloro-2, 5-bis [(2, 3-dihydroxypropyl) amino]-1-nitro-benzene (HC Red No. 11 ), 1-amino-5-chloro-4-(2, 3-dihydroxypropyl) amino-benzene (HC Red No. 10), 1-amino-2-nitro-4-(2-hydroxyethyl) amino-benzene (HC Red No. 7), 2-chloro-5-nitro-N-(2-hydroxyethyl)-1, 4-phenylendiamine, 1-[(2-hydroxyethyl)-amino]-2-nitro-4-amino-benzene (HC Red No. 3), 4-amino-2-nitrodiphenylamine (HC Red No. 1), 2-nitro-4'-hydroxy-diphenylamine (HC Orange No. 1), 1-amino-3-methyl-4-(2-hydroxyethyl)amino-6-nitrobenzene (HC Violet No. 1), 2-(2-hydroxyethyl)amino-5-(bis (2-hydroxyethyl)) amino-1-nitro-benzene (HC Blue No. 2), 1-(2-hydroxyethyl) amino-2-nitro-4-N-ethyl-N-(2-hydroxyethyl)amino-benzene (HC Blue No. 12), 4-amino-3, 5-dinitro-benzoic acid, 4-amino-2-nitrodiphenylamin-2'-carbonic acid, 2-(4'-amino-2'-nitroanilino)-benzoic acid, 6-nitro-2, 5-diaminopyridine, 2-amino-6-chloro-4-nitrophenol, 4-amino-4'-nitrostilben-2, 2'-disulfonic acid, 4'-amino-4-nitrodiphenylamin-2-sulfonic acid, 4'-amino-3'-nitrobenzophenon-2-carbonic acid, 1-amino-4-nitro-2-(2'-nitrobenzylidenamino)-benzene, 2-[2-(diethylamino) ethylamino]-5-nitroaniline, 3-amino-4-hydroxy-5-nitrobenzolsulfonic acid, 3-amino-3'-nitrobiphenyl, 3-amino-4-nitro-ace-naphthen, 2-amino-1-nitronaphthaline, 5-amino-6-nitrobenzo-1, 3-dioxol, 2-amino-6-nitrobenzothiazol, 4-(3-hydroxypropyl)amino-3-nitro-phenol (HC Red BN), 2-amino-4, 6-dinitrophenol, 3-nitro-4-(2-hydroxyethyl)-aminophenol, 2-(2-hydroxyethyl) amino-4,6-dinitrophenol, 2-amino-6-chlor-4-nitrophenol, 2-chloro-6-ethylamino-4-nitro-phenol, 1-(2-hydroxyethyl) amino-4-methyl-2-nitrobenzene, 1-(2'-ureidoethyl) amino-4-nitrobenzene, 4-amino-2-nitro-diphenylamin-2'-carbonic acid, 6-nitro-1,2,3,4-tetrahydrochinoxaline and 4-ethylamino-3-nitrobenzoic acid.

Suitable anthraquinone dyes suitable for the method of the present invention are the following compounds: 1-[(3-aminopropyl)amino]-anthraquinone (HC Red No. 7), 2-[(2-aminoethyl)amino]-anthraquinone (HC Orange No. 5), 1,4,5,8-tetraamino-anthrachinone (Disperse Blue 1), 1-[(2-Hydroxyethyl)amino]-4-methylamino-anthraquinone (Disperse Blue 3), 1,4-[(2-hydroxyethyl)amino]-5,8-dihydroxy-anthraquinone (Disperse Blue 7), 1,4-diamino-2-methoxy-anthraquinone (Disperse Red 11), 1-amino-4-hydroxy-anthraquinone (Disperse Red 15), 1,4-diamino-anthraquinone (Disperse Violet 1), 1-amino-4-methylaminoanthrachinone (Disperse Violet 4) and 1-amino-4-isopropylamino-anthraquinone (Disperse Violet 15).

Suitable azo dyes are for example the following compounds:
4-amino-4'-[bis(2-hydroxyethyl)]amino-azobenzene (Disperse Black 9), 4-amino-4'-nitroazobenzene (Disperse Orange 3), 3-hydroxy-4-[(2-hydroxy-naphth-1-yl)azo)-7-nitro-naphthalin-1-sulfonic acid-chromcomplex (Acid Black 52), 1-amino-2-(3'-nitro-phenylazo)-7-phenylazo-8-naphthol-3, 6-disulfonic acid (Acid blue Nr. 29), 1-amino-2-(2'-hydroxy-4'-nitrophenylazo)-8-naphthol-3, 6-disulfonic acid (Palatinchrome green), 1-amino-2-(3'-chlor-2'-hydroxy-5'-nitrophenylazo)-8-naphthol-3, 6-disulfonic acid (Gallion) and diamino-3', 5'-dinitro-2'-hydroxy-5-methyl-azobenzene (Mordant brown 4).

Suitable cationic dyes are the following compounds: N-[4-[[4-(diethylamino)phenyl][4-(ethylamino)-naphth-1-yl]methylene]-2,5-cyclohexadien-1-yliden]-N-ethyl-ethaniminium-chloride (Basic Blue No. 7), N-{4-[(4-(dimethylamino)phenyl) 4-(phenylamino)-1-naphthalenyl] methylene}-2, 5-cyclohexadien-1-ylidene]-N-methyl-methaniminiumchloride (Basic Blue 26), 4-[(4-aminophenyl)(4-imino-2,5-cyclohexadien-1-yliden) methyl]-2-methyl-anilin-hydrochloride (Basic Violet 14), N-{3-[(4, 5-dihydro-3-methyl-5-oxo-1-phenyl-1H-pyrazol-4-yl)azo]phenyl}-N, N, N-trimethylammoniumchloride (Basic Yellow 57), N-[7-hydroxy-8-[(2-methoxyphenyl)azo]-naphth-2-yl]-N,N,N-trimethylammonium-chloride (Basic Red 76), N-[4-[[4-(dimethylamino) phenyl][4-(phenylamino)-naphth-1-yl]-methylene]-2,5-cyclohexadien-1-yliden]-N-methyl-2-methaniminiumchloride (Basic Blue 99), [8-[(4'-amino-2'-nitrophenyl)azo]-7-hydroxy-naphth-2-yl]-trimethylammoniumchloride (Basic Brown 16), [8-((4'-amino-3'-nitrophenyl)azo)-7-hydroxy-naphth-2-yl]-trimethylammoniumchloride (BasicBrown 17), Basic Yellow 87, Basic Red 51 or Basic Orange 31.

More preferred are compounds of formula (1) or (2), wherein

W is chosen from imidazolium, pyridinium, benzimidazolium, pyrazolium, and benzothiazolium which are optionally substituted with at least one identical or different $C_1$-$C_4$alkyl.

Most preferably

W is a radical of a cationic aromatic substituted or unsubstituted heterocyclic compound of formulae

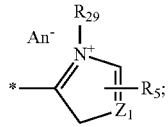
(W₁)

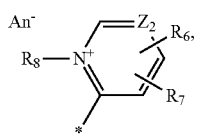
(W₂)

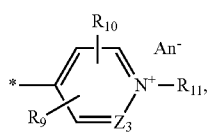
(W₃)

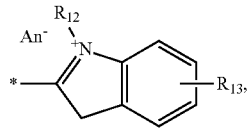
(W₄)

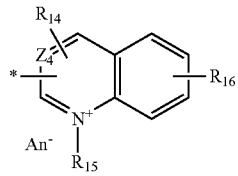
(W₅)

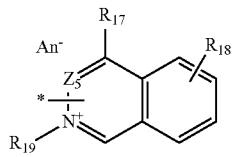
(W₆)

$Z_1$, $Z_2$, $Z_3$, $Z_4$, and $Z_5$, independently from each other N or —CH=;

$R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$ and $R_{29}$ independently from each other are hydrogen; halogen; or $C_1$-$C_{14}$ alkyl, which is saturated or unsaturated, linear or branched, substituted or unsubstituted, or interrupted or uninterrupted with heteroatoms; a radical of phenyl, which substituted or unsubstituted; a of carboxylic acid radical; sulfonic acid radical; hydroxy; nitrile; $C_1$-$C_{16}$ alkoxy, (poly)-hydroxy-$C_2$-$C_4$-alkoxy; halogen; sulfonylamino; $SR_{20}$, $NHR_{21}$; $NR_{22}R_{235}$; $OR_{24}$; $SO_2$; $COOR_{25}$; $NR_{26}COR_{27}$; or $CONR_{28}$; and $R_{20}$, $R_{21}$, $R_{22}$, $R_{23}$, $R_{24}$, $R_{25}$, $R_{26}$, $R_{271}$ and $R_{28}$ are each independently of the other hydrogen; unsubstituted or substituted $C_1$-$C_{14}$alkyl, $C_2$-$C_{14}$alkenyl, $C_5$-$C_{10}$aryl, $C_5$-$C_{10}$aryl-($C_1$-$C_{10}$alkyl), or —$C_1$-$C_{10}$alkyl($C_5$-$C_{10}$aryl); and An is an anion.

Even more ore preferred are compounds of formula (1) or (2), wherein

A is chosen from the radicals

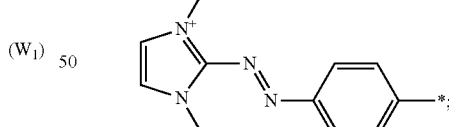

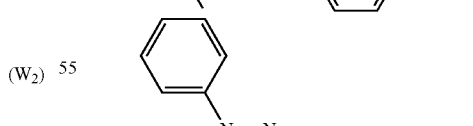

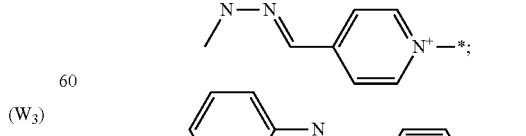

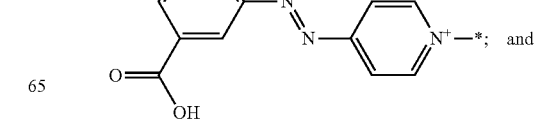
and

-continued

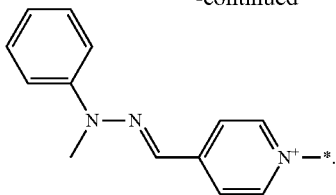

Most preferred are compounds of formula (1) wherein
A is a radical of formula (1a) W—N=N—Ar; or formula (1b) Ar—N=N—W—;
p and q and r are 1;
W is a fused or non-fused, aromatic or nonaromatic heterocycle comprising a quaternary ammonium; and
$X_1$, $X_2$, D, $C_{sat}$ and $C'_{sat}$ are defined as in formula (1).

Most preferred are compounds of formula (2) wherein
A is a radical of formula (1a) W—N=N—Ar—; or (1c) Ar—N($R_4$)—N=CH—W—;
V is —$(CH_2)_2$—;
p is 1;
q is 0;
W is a fused or non-fused, aromatic or nonaromatic heterocycle comprising a quaternary ammonium; and
$X_1$, $X_2$, $C_{sat}$, $C'_{sat}$ and $R_4$ are defined as in formula (1).

Preferred compounds according to the present invention correspond to the formula

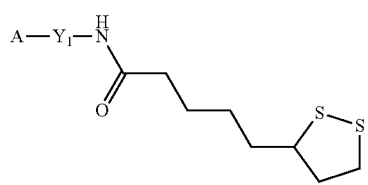

(3)

wherein
A is a radical of formula (1a) W—N=N—Ar—; or (1b) Ar—N=N—W—; and
$Y_1$ is a biradical selected from phenylene; cyclohexylene; and $C_1$-$C_3$alkylene; and
W is a fused or non-fused, aromatic or nonaromatic heterocycle comprising a quaternary ammonium; and
Ar is defined as in formula (1).

Further preferred compounds according to the present invention correspond to the compounds of formula

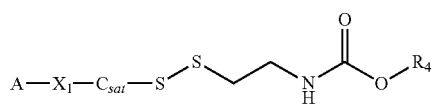

(4)

wherein
A is a radical of formula (1a) W—N=N—Ar—; or (1b) Ar—N=N—W—;
$R_4$ is methyl; or tert. butyl; and
W is a fused or non-fused, aromatic or nonaromatic heterocycle comprising a quaternary ammonium; and
$X_1$ and $C_{sat}$ are defined as in formula (1); and
Ar is defined as in formula (1c).

Most preferred are compounds of formula (3) and (4), wherein
A is a radical of formula

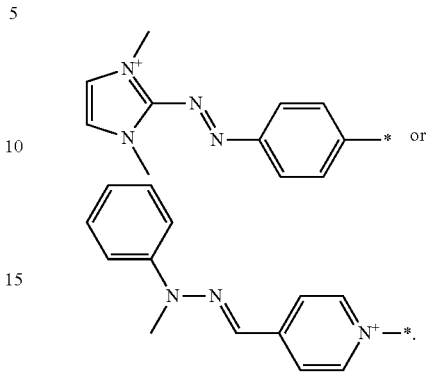

The aryl or heteroaryl radicals or the aryl or heteroaryl part of a radical may be substituted with at least one substituent carried by a carbon atom, chosen from a $C_1$-$C_{16}$, such as $C_1$-$C_8$alkyl optionally substituted with at least one radical chosen from hydroxyl, $C_1$-$C_4$alkoxy, $C_2$-$C_4$ (poly)hydroxyalkoxy, acylamino, amino substituted with two $C_1$-$C_4$alkyl, which are identical or different, optionally bearing at least one hydroxyl group, or it being possible for the two radicals to form, with the nitrogen atom to which they are attached, an optionally substituted, saturated or unsaturated heterocycle comprising from 5 to 7 members, such as 5 or 6 members, optionally comprising another heteroatom which is identical to or different from nitrogen; a halogen atom such as chlorine, fluorine or bromine; a hydroxyl group; $C_1$-$C_4$ alkoxy, a $C_2$-$C_4$ (poly)hydroxyalkoxy; amino, optionally substituted with one or two $C_1$-$C_4$alkyl, which are identical or different, optionally bearing at least one group chosen from hydroxyl and amino groups, or with two optionally substituted $C_1$-$C_3$alkyl, it being possible for the alkyl radicals to form, with the nitrogen atom to which they are attached, an optionally substituted, saturated or unsaturated heterocycle comprising from 5 to 7 members, optionally comprising at least one other heteroatom different from or identical to nitrogen; an acylamino (—NR—COR') radical in which the radical R is chosen from a hydrogen atom and $C_1$-$C_4$alkyl optionally bearing at least one hydroxyl group and the radical R' is $C_1$-$C_2$alkyl; a carbamoyl $((R)_2N$—CO—) radical in which the radicals R, which are identical or different, are chosen from hydrogen and $C_1$-$C_4$alkyl, optionally bearing at least one hydroxyl group; an alkylsulphonyl amino (R'$SO_2$—NR—) radical in which the radical R is chosen from hydrogen and $C_1$-$C_4$alkyl optionally bearing at least one hydroxyl group and the radical R' is chosen from $C_1$-$C_4$alkyl and phenyl; an aminosulphonyl $((R)_2N$—$SO_2$—)-radical in which the radicals R, which are identical or different, are chosen from a hydrogen atom and a $C_1$-$C_4$alkyl optionally bearing at least one hydroxyl group, a carboxyl radical in acid form or salified form (such as with an alkali metal or an ammonium, substituted or unsubstituted); a nitro radical; a nitrile (CN) group; a trifluoromethyl ($CF_3$) group; the cyclic or heterocyclic part of a nonaromatic radical may be substituted with at least one substituent carried by a carbon atom chosen from the groups: hydroxyl, $C_1$-$C_4$alkoxy, $C_2$-$C_4$(poly)hydroxyalkoxy, alkylcarbonylamino (RCO—NR'—) in which R' is chosen from a hydrogen atom and $C_1$-$C_4$alkyl optionally bearing at least one hydroxyl group and the radical R is $C_1$-$C_2$alkyl, an amino radical substituted with two $C_1$-$C_4$alkyl groups which are identical or different, optionally bearing at least one hydroxyl group, it being possible for the alkyl radicals to form, with the nitrogen atom to which they are attached, an optionally substituted, saturated or unsaturated heterocycle comprising from 5 to 7 members, optionally comprising at least one other heteroatom different from or identical to nitrogen; a hydrocarbon chain is unsaturated when it contains one or more double bonds and/or one or more triple bonds; a heteroaromatic or heteroaryl radical is an aromatic radical in which at least one of the carbon atoms is replaced by a heteroatom chosen from nitrogen, oxygen and sulphur.

The residue of an organic dye is preferably selected from the group of anthraquinone, acridine, azo, azomethine, hydrazomethine, benzodifuranone, coumarine, diketopyrrolopyrrol, dioxaxine, diphenylmethane, formazan, indigoid, indophenol, naphthalimide, naphthoquinone, nitroaryl, merocyanine, methin, oxazine, perinone, perylene, pyrenequinone, phtalocyanine, phenazine, quinoneimine, quinacridone, quinophtalone, styryl, triphenylmethane, xanthene, thiazine and thioxanthene dye.

Examples of the disulfide dyes of the present invention are listed below:

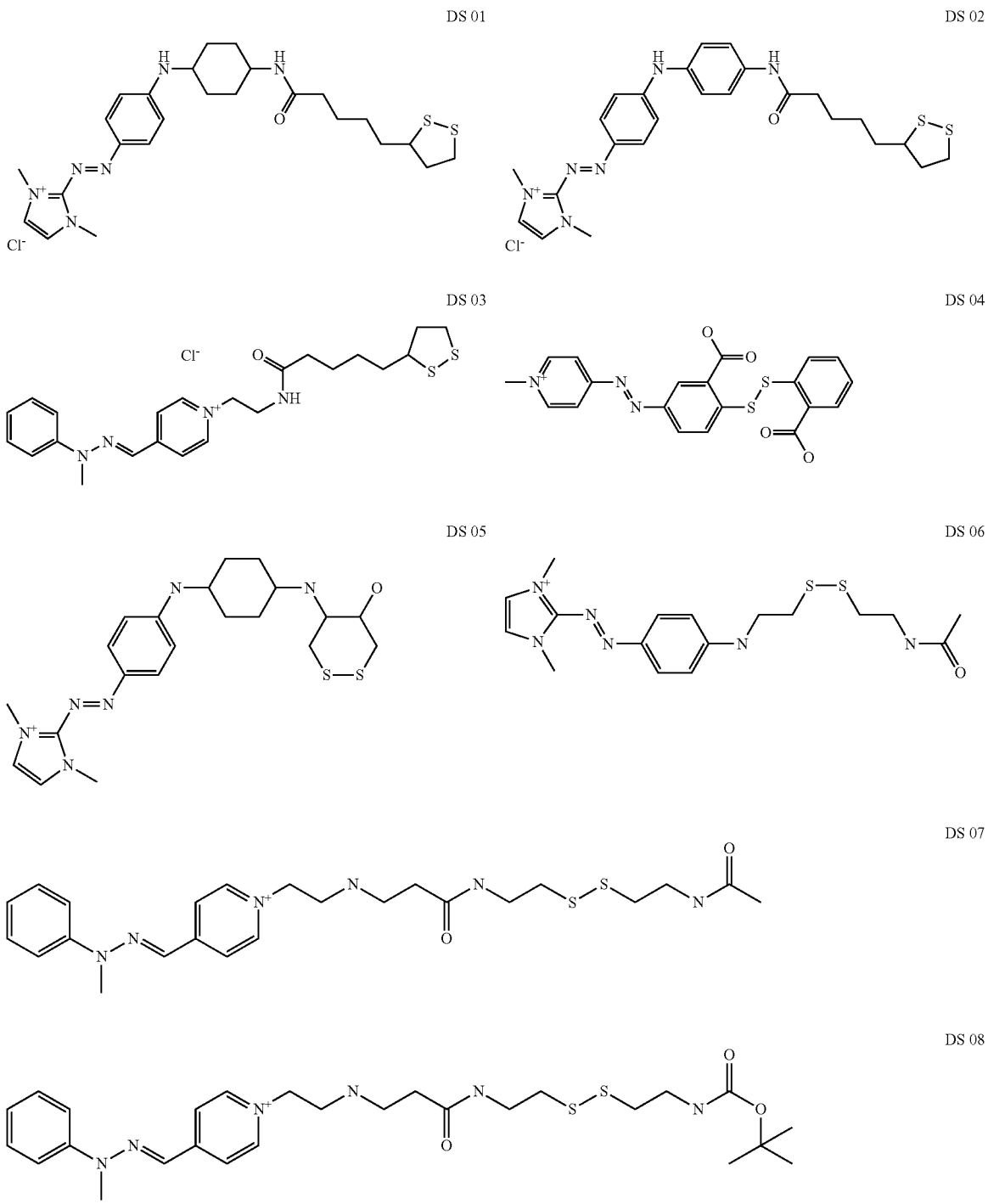

The dyeing composition useful in the method of the present invention may comprise at least one disulfide dye chosen from the dyes of formulae (1) and (2).

The at least one disulfide dye may be present in the composition in an amount ranging from 0.001 to 50% relative to the total weight of the composition. In at least one embodiment, this amount ranges from 0.005 to 20% by weight, such as from 0.01 to 5% by weight relative to the total weight of the composition.

The dyes of formula (1) and (2) according to the invention are suitable for dyeing organic materials, such as keratin-containing fibers, wool, leather, silk, cellulose or polyamides, cotton or nylon, and preferably human hair. The dyeings obtained are distinguished by their depth of shade and their good fastness properties to washing, such as, for example, fastness to light, shampooing and rubbing. The stability, in particular the storage stability of the dyes according to the invention are excellent.

The multiplicity of shades of the dyes can be increased by combination with other dyes.

Therefore the dyes of formula (1) and (2) of the present invention may be combined with dyes of the same or other classes of dyes, especially with direct dyes, oxidation dyes; dye precursor combinations of a coupler compound as well as a diazotized compound, or a capped diazotized compound; and/or cationic reactive dyes.

Direct dyes are of natural origin or may be prepared synthetically. They are uncharged, cationic or anionic, such as acid dyes.

The dyes of formula (1) and (2) may be used in combination with at least one single direct dye different from the dyes of formula (1) and (2).

Examples of direct dyes are described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, and in "Europäisches Inventar der Kosmetikrohstoffe", 1996, published by The European Commission, obtainable in diskette form from the Bundesverband der deutschen Industrie-und Handelsunternehmen für Arzneimittel, Reformwaren und Körperpflegemittel e.V., Mannheim.

Furthermore, cationic nitroaniline and anthraquinone dyes are useful for a combination with a dye of formula (1) and (2).

The dyes of formula (1) and (2) may also be combined with acid dyes, for example the dyes which are known from the international names (Color index), or trade names.

These acid dyes may be used either as single component or in any combination thereof.

The dyes of formula (1) and (2) may also be combined with uncharged dyes, for example selected from the group of the nitroanilines, nitrophenylenediamines, nitroaminophenols, anthraquinones, indophenols, phenazines, phenothiazines, bispyrazolons, bispyrazol aza derivatives and methines.

Furthermore, the dyes of formula (1) and (2) may also be used in combination with oxidation dye systems.

Oxidation dyes, which, in the initial state, are not dyes but dye precursors are classified according to their chemical properties into developer and coupler compounds.

Suitable oxidation dyes are described for example in
DE 19 959 479, especially in col 2, l. 6 to col 3, l. 11;
"Dermatology", edited by Ch. Culnan, H. Maibach, Verlag Marcel Dekker Inc., New York, Basle, 1986, Vol. 7, Ch. Zviak, The Science of Hair Care, chapter 8, on p. 264-267 (oxidation dyes).

Preferred developer compounds are for example primary aromatic amines, which are substituted in the para- or ortho-position with a substituted or unsubstituted hydroxy- or amino residue, or diaminopyridine derivatives, heterocyclic hydrazones, 4-aminopyrazol derivatives or 2,4,5,6-tetraaminopyrimidine derivatives.

Furthermore, developer compounds in their physiological compatible acid addition salt form, such as hydrochloride or sulfate can be used. Developer compounds, which have aromatic OH radicals are also suitable in their salt form together with a base, such as alkali metalphenolates.

Preferred developer compounds are disclosed in DE 19959479, p. 2, l. 8-29.

Preferred coupler compounds are m-phenylendiamine derivatives, naphthole, resorcine and resorcine derivatives, pyrazolone and m-aminophenol derivatives, and most preferably the coupler compounds disclosed in DE 19959479, p.1, l. 33 to p. 3, l. 11.

Furthermore, autooxidizable compounds may be used in combination with the dyes of formula (1).

Autooxidizable compounds are aromatic compounds with more than two substituents in the aromatic ring, which have a very low redox potential and will therefore be oxidized when exposed to the air. The dyeings obtained with these compounds are very stable and resistant to shampoo.

Autooxidizable compounds are for example benzene, indole, or indole, especially 5,6-dihydroxyindol or 5,6-dihydroxyindol.

The dyes of formula (1) may also be used in combination with naturally occurring dyes, such as henna red, henna neutral, henna black, camomile blossom, sandalwood, black tea, Rhamnus frangula bark, sage, campeche wood, madder root, catechu, sedre and alkanet root.

Furthermore, the dyes of formula (1) and (2) may also be used in combination with capped diazotized compounds.

Suitable diazotized compounds are for example the compounds of formulae (1)-(4) in WO 2004/019897 (bridging gages 1 and 2) and the corresponding water-soluble coupling components (I)-(IV) as disclosed in the same reference on p. 3 to Further preferred dyes or dye combinations which are useful for the combination with a dye of formula (1) according to the present invention are described in (DC-01): WO 95/01772, wherein mixtures of at least two cationic dyes are disclosed, especially p. 2, l. 7 to p. 4, l. 1, preferably p. 4, l. 35 to p. 8, l. 21; formulations p. 11, last §-p. 28, l. 19;

(DC-02): U.S. Pat. No. 6,843,256, wherein cationic dyes are disclosed, especially the compounds of formulae (1), (2), (3) and (4) (col. 1, l. 27-col. 3, l. 20, and preferably the compounds as prepared in the examples 1 to 4 (col. 10, l. 42 to col. 13, l. 37; formulations col. 13, l. 38 to col. 15, l. 8;

(DC-03): EP 970 685, wherein direct dyes are described, especially p. 2, l. 44 to p. 9, l. 56 and preferably p. 9, l. 58 to p. 48, l. 12; processes for dyeing of keratin-containing fibers especially p. 50, l. 15 to 43; formulations p. 50, l. 46 to p. 51, l. 40;

(DC-04): DE-A-19 713 698, wherein direct dyes are described, especially p. 2, l. 61 to p. 3, l. 43; formulations p. 5, l. 26 to 60;

(DC-05): U.S. Pat. No. 6,368,360, wherein directed dyes (col. 4, l. 1 to col. 6, l. 31) and oxidizing agents (col. 6, l. 37-39) are disclosed; formulations col. 7, l. 47 to col. 9, l. 4;

(DC-06): EP 1 166 752, wherein cationic dyes (p. 3, l. 22-p. 4, l. 15) and anionic UV-absorbers (p. 4, l. 27-30) are disclosed; formulations p. 7, l. 50-p. 9, l. 56;

(DC-07): EP 998,908, wherein oxidation dyeings comprising a cationic direct dye and pyrazolo-[1,5-a]pyrimidines (p. 2, l. 48-p. 4, l. 1) are disclosed; dyeing formulations p. 47, l. 25 to p. 50, l. 29;

(DC-08): FR-2788432, wherein combinations of cationic dyes with Arianors are disclosed, especially p. 53, l. 1 to p. 63, l. 23, more especially p. 51 to 52, most especially Basic Brown 17, Basic brown 16, Basic Red 76 and Basic Red 118, and/or at least one Basic Yellow 57, and/or at least one Basic Blue 99; or combinations of arianors and/or oxidative dyes, especially p. 2, l. 16 to p. 3, l. 16; dyeing formulations on p. 53, l. 1 to p. 63, l. 23;

(DC-09): DE-A-19 713 698, wherein the combinations of direct dyes and permanent-wave fixing comprising an oxidation agent, an oxidation dye and a direct dye are disclosed; especially p. 4, l. 65 to p. 5, l. 59;

(DC-10): EP 850 638, wherein developer compounds and oxidizing agents are disclosed; especially p. 2, l. 27 to p. 7, l. 46 and preferably p. 7, l. 20 to p. 9, l. 26; dyeing formulations p. 2, l. 3-12 and l. 30 to p. 14, and p. 28, l. 35-p. 30, l. 20; preferably p. 30, l. 25 p. 32, l. 30; (DC-11): U.S. Pat. No. 6,190,421 wherein extemporaneous mixtures of a composition (A) containing one or more oxidation dye precursors and optionally one or more couplers, of a composition (B), in powder form, containing one or more direct dyes (col. 5, l. 40-col. 7, l. 14), optionally dispersed in an organic pulverulent excipient and/or a mineral pulverulent excipient, and a composition (C) containing one or more oxidizing agents are disclosed; formulations col. 8, l. 60-col. 9, l. 56;

(DC-12): U.S. Pat. No. 6,228,129, wherein a ready-to-use composition comprising at least one oxidation base, at least one cationic direct dye and at least one enzyme of the 2-electron oxidoreductase type in the presence of at least one donor for the said enzyme are disclosed; especially col. 8, l. 17-col. 13, l. 65; dyeing formulations in col. 2, l. 16 to col. 25, l. 55, a multi-compartment dyeing device is described in col. 26, l. 13-24;

(DC-13): WO 99/20235, wherein compositions of at least one cationic dye and at least one nitrated benzene dye with cationic direct dyes and nitro benzene direct dyes are described; on p. 2, l. 1 to p. 7, l. 9, and p. 39, l. 1 to p. 40 l. 11, preferably p. 8, l. 12 to p. 25 l. 6, p. 26, l. 7 to p. 30, l. 15; p. 1, l. 25 to p. 8, l. 5, p. 30, l. 17 to p. 34 l. 25, p. 8, l. 12 to p. 25 l. 6, p. 35, l. 21 to 27, especially on p. 36, l. 1 to p. 37;

(DC-14): WO 99/20234, wherein compositions comprising at least one direct cationic dye and at least one autooxidisable dye, especially benzene, indole and indole. derivatives are described, preferably direct dyes on p. 2, l. 19 to p. 26, l. 4, and autooxidizable dyes as disclosed especially on p. 26, l. 10 to p. 28, l. 15; dyeing formulations especially on p. 34, l. 5 to p. 35, li 18;

(DC-15): EP 850 636, wherein oxidation dyeing compositions comprising at least one direct dye and at least one meta-aminophenol derivative as coupler component and at least one developer compound and an oxidizing agent are disclosed, especially p. 5, l. 41 to p. 7, l. 52, dyeing formulations p. 19, l. 50-p. 22, l. 12;

(DC-16): EP-A-850 637, wherein oxidation dyeing compositions comprising at least one oxidation base selected from para-phenylenediamines and bis(phenyl)alkylenediamines, and the acid-addition salts thereof, at least one coupler selected from meta-diphenols, and the acid-addition salts thereof, at least one cationic direct dye, and at least one oxidizing agent are disclosed, especially p. 6, l. 50 to p. 8, l. 44 are disclosed; dyeing formulations p. 21, l. 30-p. 22, l. 57;

(DC-17): WO 99/48856, wherein oxidation dyeing compositions comprising cationic couplers are disclosed, especially p. 9, l. 16-p. 13, l. 8, and p. 11, l. 20-p. 12, l. 13; dyeing formulations p. 36, l. 7-p. 39, l. 24;

(DC-18): DE 197 172 24, wherein dyeing agents comprising unsaturated aldehydes and coupler compounds and primary and secondary amino group compounds, nitrogen-containing heterocyclic compounds, amino acids, oligopeptids, aromatic hydroxy compounds, and/or at least one CH-active compound are disclosed p. 3, l. 42-p. 5 l. 25; dyeing formulations p. 8, l. 25-p. 9, l. 61.

In the dye combinations disclosed in the references (DC-01-DC-18) above, the dyes of formula (1) according to the present invention may be added to the dye combinations or dyeing formulations or may be replaced with at least one dye of formula (1).

The dyeing composition may further comprise at least one oxidation base and/or at least one coupler conventionally used for dyeing keratin fibers.

Among the oxidation bases, mention may be made of par-aphenylenediamines, bisphenylalkylenediamines, para-aminophenols, bis-para-aminophenols, ortho-aminophenols, heterocyclic bases and their addition salts.

Among the couplers, there may be mentioned meta-phenylenediamines, meta-aminophenols, meta-diphenols, naphthalene couplers, heterocyclic couplers and their addition salts.

The coupler(s) is (are) each generally present in an amount ranging from 0.001 to 10% by weight relative to the total weight of the dyeing composition, such as from 0.005 to 6%.

The oxidation base(s) present in the dyeing composition is (are) in general each present in an amount ranging from 0.001 to 10% by weight relative to the total weight of the dyeing composition, such as from 0.005 to 6% by weight.

In general, the addition salts of the oxidation bases and couplers which can be used in the context of the present invention are chosen, for example, from addition salts with an acid, such as the hydrochlorides, hydrobromides, sulphates, citrates, succinates, tartrates, lactates, tosylates, benzenesulphonates, phosphates and acetates, and addition salts with a base, such as the alkali metal hydroxides such as sodium hydroxide or potassium hydroxide, aqueous ammonia, amines or alkanolamines.

The appropriate medium for dyeing, also called the dye support, is a cosmetic medium which generally comprises water or a mixture of water and at least one organic solvent.

As organic solvent, mention may be made for example of lower $C_1$-$C_4$ alkanols such as ethanol and isopropanol; polyols and polyol ethers such as 2-butoxyethanol, propylene glycol, propylene glycol monomethyl ether, diethylene glycol monoethyl ether and monomethyl ether, and aromatic alcohols such as benzyl alcohol or phenoxyethanol, and mixtures thereof.

The solvents, when they are present, may be present in an amount ranging from 1 to 40% by weight relative to the total weight of the dyeing composition, such as from 5 to 30% by weight.

The dyeing composition may also comprise at least one adjuvant conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickening agents, such as anionic, cationic, nonionic and amphoteric associative polymeric thickeners, antioxidants, penetration agents, sequestering agents, perfumes, buffers, dispersing agents, conditioning agents such as for example modified or unmodified, volatile or nonvolatile silicones, film forming agents, ceramides, preservatives and opacifiers.

The above adjuvants are generally present in an amount for each of them of from 0.01 to 20% by weight relative to the weight of the composition.

The composition may also comprise at least one other additional disulphide compound different from that corresponding to formulae (1) or (2).

As a guide, the disulphide may be chosen from compounds comprising at least one fatty chain, such as at least one saturated or unsaturated, linear or branched $C_5$-$C_3$ hydrocarbon chain which is optionally substituted with a heteroatom and optionally interrupted by a neutralized or nonneutralized carboxyl group.

Byway of example of compounds of this type, mention may be made of the dimers of thioglycolic acid and its derivatives of the $CH_3$—$(CH_2)1_7$-S—S—$(CH2)_{17}$-$CH_3$ or $CH_3$—$(CH_2)$—S—S—$(CH_2)_{10}$—$CH_3$ type.

If it is present, the at least one additional disulphide compound is present in an amount ranging from 0.001 to 10% by weight relative to the weight of composition.

Of course, persons skilled in the art will be careful to choose this or these optional additional compounds such that the advantageous properties intrinsically attached to the dyeing composition in accordance with the invention are not, or not substantially, impaired by the addition(s) envisaged.

The pH of the dyeing composition may range from 3 to 14, such as from 5 to 11. It may be adjusted to the desired value by means of acidifying or alkalinizing agents customarily used for dyeing keratin fibers, or alternatively with the aid of conventional buffer systems. Among the acidifying agents, there may be mentioned, by way of example, inorganic or organic acids such as hydrochloric acid, orthophosphoric acid, sulphuric acid, carboxylic acids such as acetic acid, tartaric acid, citric acid, lactic acid and sulphonic acids.

Among the alkalinizing agents, there may be mentioned, by way of example, aqueous ammonia, alkali metal carbonates, alkanolamines such as mono-, di- and triethanolamines and derivatives thereof, sodium or potassium hydroxides and compounds of the following formula

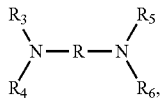

wherein
R is a propylene residue, which may be substituted with OH or $C_1$-$C_4$alkyl,
$R_3$, $R_4$, $R_5$ and $R_6$ are independently or dependently from each other hydrogen, $C_1$-$C_4$alkyl or hydroxy-($C_1$-$C_4$)alkyl.

The dyeing composition may be provided in various forms, such as in the form of a liquid, a cream, a gel, or in any other appropriate form for dyeing keratin fibers, such as the hair.

According to one embodiment, the method of the invention comprises a pretreatment with a reducing agent capable of reducing the disulphide bond.

The reducing agent is chosen, for example, from thiols, for example thioglycolic acid, cysteine, homocysteine, thiolactic acid, the salts of these thiols, phosphines, bisulphite and sulphites.

This reducing agent may also be chosen from borohydrides and derivatives thereof, such as, for example, the borohydride, cyano borohydride, triacetoxyborohydride and trimethoxy borohydride salts: sodium, lithium, potassium, calcium and quaternary ammonium (tetramethylammonium, tetraethyl ammonium, tetra-n-butyl ammonium, benzyltriethylannnonium) salts; catecholborane.

This pretreatment may be of a short duration, from 0.1 second to 30 minutes, for example from 0.1 second to 5 minutes, with a reducing agent as mentioned above.

The application of the dyeing composition is generally carried out at room temperature. It may however be carried out at temperatures ranging from 20 to 100 C.

According to one embodiment, the reducing agent is added to the dyeing composition at the time of use.

According to another embodiment, the application of the dyeing composition may be followed by a short reducing step of 0.1 second to 30 minutes, such as from 0.1 second to 5 minutes, with a reducing agent of the thiol or borohydride type as described above.

According to another embodiment, the dyeing composition may comprise at least one oxidizing agent; the composition is then said to be "ready-to-use."

In at least one embodiment, the composition is obtained by mixing the composition according to the disclosure with an oxidizing composition before application to the keratin materials to be treated.

The oxidizing agent may be any oxidizing agent conventionally used in the field. Thus, it may be chosen from hydrogen peroxide, urea peroxide, alkali metal bromates, per salts such as perborates and persulphates, and enzymes, among which mention may be made of peroxidases, oxidoreductases containing 2 electrons such as uricases, and oxygenases containing 4 electrons such as laccases. In at least one embodiment, the oxidizing agent is hydrogen peroxide.

The amount of oxidizing agent in the composition ranges from 1 to 40% by weight relative to the weight of the ready-to-use composition, such as from 1 to 20% by weight relative to the weight of the ready-to-use composition.

Generally, the oxidizing composition used is an aqueous composition and may be in the form of a solution or also an emulsion.

Customarily, the dyeing composition, free of oxidizing agent, is mixed with 0.5 to 10 equivalents by weight of the oxidizing composition.

It should be noted that the pH of the ready-to-use composition is, for example, from 4 to 12, such as from 7 to 11.5.

The application of the dyeing composition may be followed by an oxidizing post-treatment, or by a conditioning post-treatment optionally combined with an oxidizing post-treatment Also disclosed herein is a multi-compartment device or dyeing "kit" in which a first compartment comprises a dyeing composition comprising at least one disulphide dye of formulae
(1) or (2) and a second compartment comprises a reducing agent capable of reducing the disulphide bond of the dye.

One of these compartments may additionally comprise at least one other dye chosen from direct dyes and oxidation dyes provided that the disulphide dye which is useful herein and the at least one other dye are not in the same compartments of the kit.

The present invention also relates to a multi compartment device in which a first compartment comprises a dyeing composition comprising at least one disulphide dye of formula (1) or (2); a second compartment comprises a reducing agent capable of reducing the disulphide bond of the dye; a third compartment comprises an oxidizing agent.

Each of the abovementioned devices may be equipped with a means which makes it possible to deliver the desired mixture to the hair, for example such as the devices described in FR 2586913.

The following Examples serve to illustrate the processes for dyeing without limiting the processes thereto. Unless specified otherwise, parts and percentages relate to weight. The amounts of dye specified are relative to the material being colored.

T, s, d, q and J, wherein t is a triplet, s is singlet, d is duplet, q is a quartet, and J is a coupling constant, define the NMR-spectra values.

A. PREPARATION EXAMPLES

Example A1

An orange suspension of 1.1 g of Z-9448 (MW: 342.38) and 11.4 g of 1,4-diaminocyclohexane in 40 ml 2-propanol is stirred at 60° C. for 5 hours. After cooling at room temperature, the dark red solution is diluted with 100 ml of 2-propanol and filtered. The isopropanol solution is precipitated with 600 ml of t-butylmethylether, washed with TBME and dried at 50° C., giving 5.23 g of compound 1.

LC-MS: m/z=501; $\lambda_{max}$=514 nm

To a suspension of 0.5 g of lipoïc acid (206.33) in 4 ml of dichloromethane are added 0.34 g of thionyl chloride (MW: 118.97). The reaction mixture becomes soluble. After one hour stirring at room temperature, the yellow solution is added to a solution of 0.84 g of compound 1 (MW: 348.88) and 0.72 g of triethylamine (MW: 101.19) in 30 ml of dimethylacetamide at 40° C. After 2 hours stirring at 40° C. the reaction mixture is cooled down to room temperature and precipitated in 150 ml of ethyl acetate. The dark red powder is dried at 50° C. The product 2 is purified by column chromatography.

Example A2

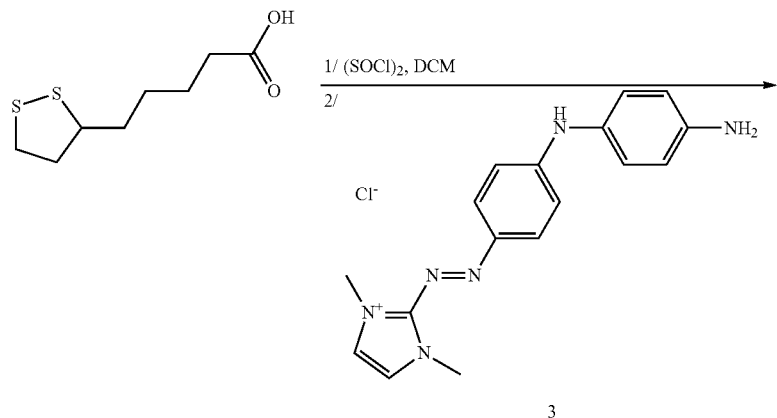

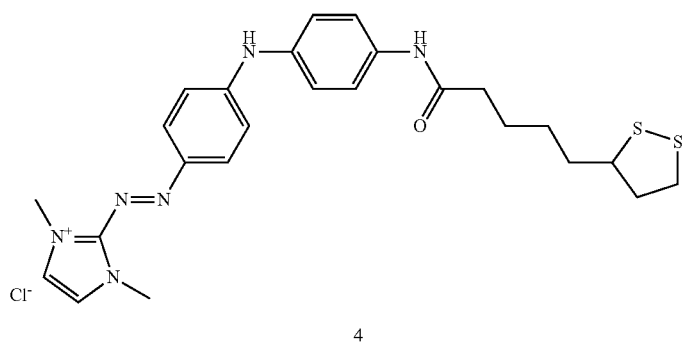

178822-03-2 (compound 3) is prepared as described in EP 1 219683

To a suspension of 0.32 g of lipoïc acid (206.33) in 4 ml of dichloromethane are added 0.24 g of thionyl chloride (MW: 118.97). The reaction mixture becomes soluble. After one hour stirring at room temperature, the yellow solution is added to a solution of 0.31 g of compound 3 (MW: 307.38) in 20 ml of dimethylacetamide at 40° C. After 2 hours stirring at 40° C. the reaction mixture is cooled down to room temperature and precipitated in 150 ml of ethyl acetate. The dark powder is dried at 50° C. The product is purified by column chromatography, giving 280 mg of a dark sticky product.

LC-MS: m/z=495; $\lambda_{max}$=526 nm

Example A3

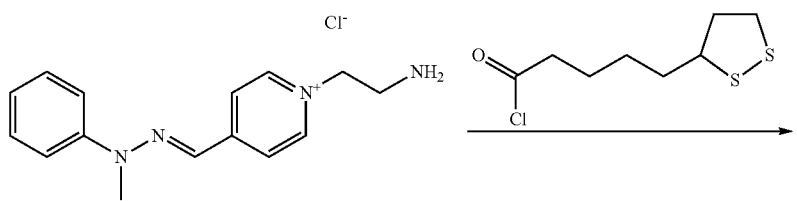

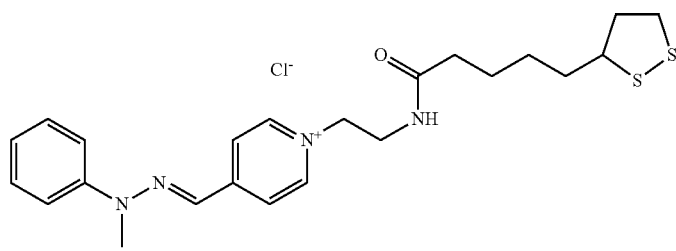

2,063 g of lipoïc acid (MW 206.33) are solubilized in 10 ml of DCM and cooled in a bath of ice and acetone. 1.13 g of thionyl chloride (MW 118.97) are added drop wise over 30 min at −8° C. The reaction mixture is stirred at room temperature for one hour. In a second flask, 1.64 g of compound 7 (MW 327.26) are solubilised in 25 ml DMI and 4,048 g of triethylamine (MW 101.19) are added. The solution of lipoïc acid chloride described above is added over 10 minutes and the reaction mixture is stirred for 90 minutes at room temperature. The reaction mixture is precipitated with 200 ml of acetone and filtrated. The filtrate is taken in 2 ml DMI, dried with sodium sulfate and recrystallized in 100 ml acetone yielding 1.96 g product 8.

LC-MS: m/z=445; $\lambda_{max}$=422 nm

Example A4

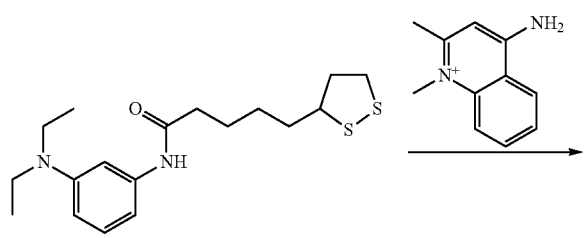

9

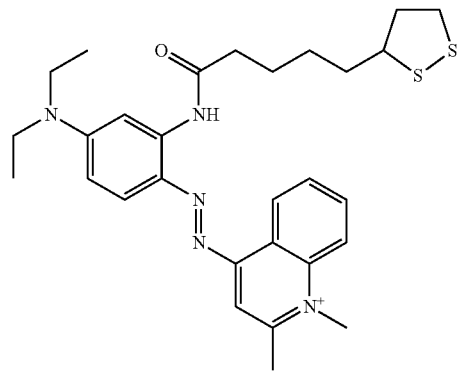

10

To a suspension of 2.06 g of lipoïc acid (206.33) in 20 ml of dichloromethane under nitrogen atmosphere are added 1.54 g of thionyl chloride (MW: 118.97). The reaction mixture becomes soluble. After one hour stirring at room temperature, the yellow solution is added to a solution of 1.65 g of N,N diethyl-benzene-1,3 diamine (CAS: 26513-20-2) (MW 164.25) in 10 ml THF. The reaction mixture is cooled to 10° C. and 3.3 g of triethylamine are added drop wise within 15 minutes. The reaction mixture is then let warm up to room temperature, is diluted with 50 ml of dichloromethane and extracted with 50 ml aqueous HCl 5%. The organic phase is dried with sodium sulphate and evaporated to dryness giving 2.9 g of the expected compound 9.

1.4 g of 4-amino-1,2-dimethyl-quinolinium (MW 284.43) are solubilised in 15 ml of formic acid and 20 ml of acetic acid. 1.4 g of nitric sulphuric acid 40% (MW 127.1) are added drop wise at 0 to 5° C. within 5 minutes. After 2 h diazotation at 0° C., the reaction mixture is dark yellow. This solution is added slowly to a solution of 1.76 g of compound 9 in 30 ml NMP at 0° C. and is let stirring at this temperature for 2 hours. 15 ml of sodium hydroxide 4N are then added and left over night. The dark blue suspension is filtered and washed with water/methanol (1/1).

The mixture is purified by filtration on silica gel (eluant THF/methanol 1/5). 100 mg of a dark sticky product 10 is obtained.

LC-MS: m/z=536; $\lambda_{max}$=596 nm

B. APPLICATION EXAMPLES

In the following application examples compositions within the below given definitions are used:
Solution 1 (Permanent Lotion, pH 8.2):
Aqua, Ammonium Thioglycolate, Ammonium Bicarbonate, Ethoxydiglycol, Hexylene Glycol, Thioglycolic Acid; Thiolactic Acid, PEG-60 Hydrogenated Castor Oil, Glycine, Etidronic Acid, Isoceteth-20, Polysilicone-9, Styrene/PVP Copolymer, Trideceth-12, Amodimethicone, Cetrimonium Chloride, Ammonium Hydroxide, Polyquaternium-6, Isopropyl Alcohol, Alcohol denat., Simethicone, Perfume
Solution 2 (Permanent Fixation, pH 3.9):
Based On:
Aqua, Hydrogen Peroxide, Propylene Glycol, Lauryldimonium Hydroxypropyl Hydrolyzed Wheat Protein, PEG-5 Cocamide, Sodium Cocoamphoacetate, Polyquaternium-35, CocoBetaine, Acetaminophen, Phosphoric Acid, Sodium Chloride, Perfume

Example B1

0.2% (abs.) of the dye A1 is dissolved in a 5% solution of a non-ionic surfactant (Plantacare 200UP, Henkel) adjusted to pH 9.5 using citric acid and monoethanolamine. This red dyeing solution is applied on the dry hair (two blond, two damaged and two 90% gray hair strands) and allowed to stand for 20 min. at room temperature. Then, the strands are rinsed under tap water and dried 12 hours.

Example B2

Solution 1 (permanent lotion) is applied on shampooed hair (two blond, two damaged and two 90% gray hair strands) and allowed to stand for 10 min. Then, the strands are rinsed under tap water, and the towel dry strands are treated with the 0.2%, by weight coloring material solution of example B1 allowed to stand for 20 min and then rinsed. Then, the towel dry strands are treated with the solution 2 (permanent fixation) and allowed to stand for 10 min. Then the strands are rinsed under tap water and dried 12 hours at room temperature.

Example B3

0.1% (abs.) of the dye A2 is dissolved in a 5% solution of a non-ionic surfactant (Plantacare 200UP, Henkel) adjusted to pH 9.5 using citric acid and monoethanolamine. This red dyeing solution is applied on the dry hair (two blond, two middle blond, two damaged and two 90% gray hair strands) and allowed to stand for 20 min. at room temperature. Then, the strands are rinsed under tap water and dried 12 hours.

Example B4

Solution 1 (permanent lotion) is applied on shampooed hair (two blond, two middle blond, two damaged and two 90% gray hair strands) and allowed to stand for 10 min. Then, the strands are rinsed under tap water, and the towel dry strands are treated with the 0.2%, by weight coloring material solution of example B1 allowed to stand for 20 min and then rinsed. Then, the towel dry strands are treated with the solution 2 (permanent fixation) and allowed to stand for 10 min. Then the strands are rinsed under tap water and dried 12 hours at room temperature.

| Assay | hair type | color | intensity | brilliance | dE* washing fastness 10x washed with shampoo | comment |
|---|---|---|---|---|---|---|
| A1 | blond | red | good | good | 21,3 | Example B1 |
|  | gray 90% | red | good | good | 20,3 | Example B1 |
|  | blond | red | good | good | 7,6 | Example B2 |
|  | gray 90% | red | good | good | 9,2 | Example B2 |
| A2 | blond | magenta | moderate | moderate | 17,1 | Example B3 |
|  | gray 90% | magenta | moderate | moderate | 14,4 | Example B3 |
|  | blond | magenta | moderate | moderate | 5,6 | Example B4 |
|  | gray 90% | magenta | moderate | moderate | 8,2 | Example B4 |

Example B5

50 parts of chemically bleached beech sulfite are mixed with 50 parts of bleached RKN 15 (freeness 22 DEG SR) and 2 parts of the dye according to Example A1 in water (pH 6, hardness of water 10 DEG of German hardness, temperature 20 DEG and liquor ratio 40:1). After stirring for 15 minutes, paper sheets are produced on a Frank sheet-former. The paper has been dyed in a very intense red shade. The effluent is completely colorless. A degree of exhaustion of virtually 100 percent is attained. The fastness properties to light and wet processing are excellent.

Example B6

A paper web composed of bleached beech sulfite pulp (22 DEG SR) is produced on a continuously operating laboratory paper-making machine. An aqueous solution of the dye according to Example A2 is metered continuously into the low-density pulp 10 seconds upstream of the head box, with vigorous turbulence (0.5 percent dyeing, liquor ratio 400:1, hardness of water 10 DEG German hardness, pH 6, temperature 20 DEG).

A deep magenta coloration of medium intensity is formed on the paper web. The effluent is completely colorless.

Example B7

10 parts of cotton fabric (bleached, mercerized cotton) are dyed in a laboratory beam dyeing machine in 200 parts of a liquor (hardness of water 10 DEG German hardness, pH 4, dye liquor circulated three times per minute) containing 0.05 part of the dye according to Example A1. The temperature is raised in the course of 60 minutes from 20 DEG to 100 DEG and is then kept constant for 15 minutes.

The dye liquor is completely exhausted. A deep red coloration distinguished by good fastness to light and very good fastness to wet processing is formed on the cotton fabric. A textile fabric composed of regenerated (viscose) is dyed by the same procedure. A deep red dyeing which has good fastness to light and very good fastness to wet processing is also obtained on this material by means of the dye of Example A 1.

Example B 8 of a Purely Solvent-containing Wood Stain 3.0 parts by weight of the dye A 1
40.0 parts by weight of ethyl alcohol,
40.0 parts by weight of 1 methoxy-2-propanol and
17.0 parts by weight of isopropanol Example B9 of an Aqueous Wood Stain 3.0 parts by weight of the dye A1 are dissolved in 100.0 ml of water containing 0.05 percent by weight Invadin LU (a wetting agent).

The wood stains obtained according to the above Example B8 and B9 are applied by means of a brush to a 10.times.5.5 cm piece of ash wood. The colored piece of wood is dried in air for 12 hours.

The invention claimed is:
1. Compounds of formula

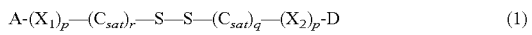

or formula

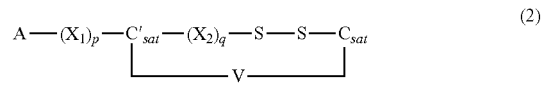

wherein
A is a radical of formula (1a) W—N═N—Ar—; (1b) Ar—N═N—W—; or (1c) Ar—N(R$_4$)—N═CH—W—
wherein W is a radical of a cationic aromatic substituted or unsubstituted heterocyclic compound of formulae

-continued

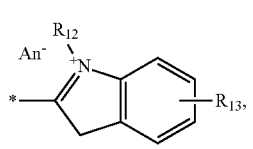
(W4)

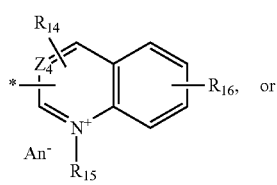
(W5)

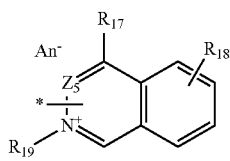
(W6)

$Z_1, Z_2, Z_3, Z_4$ and $Z_5$, independently from each other N or —CH—; $R_5, R_6, R_7, R_8, R_9, R_{10}, R_{11}, R_{12}, R_{13}, R_{14}, R_{15}, R_{16}, R_{17}, R_{18}, R_{19}$ and $R_{29}$ independently from each other are hydrogen; halogen; or $C_1-C_{14}$alkyl, which is saturated or unsaturated, linear or branched, substituted or unsubstituted, or interrupted or uninterrupted with heteroatoms; a radical of phenyl, which substituted or unsubstituted; a of carboxylic acid radical; sulfonic acid radical; hydroxy; nitrile; $C_1-C_{16}$alkoxy, (poly)-hydroxy-$C_2-C_4$-alkoxy; halogen; sulfonylamino; $SR_{20}$, $NHR_{21}$; $NR_{22}R_{23}$; $OR_{24}$; $SO_2$; $COOR_{25}$; $NR_{26}COR_{27}$; or $CONR_{28}$; and $R_{20}, R_{21}, R_{22}, R_{23}, R_{24}, R_{25}, R_{26}, R_{27}$ and $R_{28}$ are each independently of the other hydrogen; unsubstituted or substituted $C_1-C_{14}$alkyl, $C_2-C_{14}$alkenyl, $C_5-C_{10}$aryl- $C_5-C_{10}$aryl-$(C_1-C_{10}$alkyl), or —$C_1-C_{10}$alkyl($C_5-C_{10}$aryl);

An is an anion;

Ar is $C_5$ or $C_6$ aryl radicals and aromatic bicycles of the naphthyl type, which are optionally substituted with at least one halogen atom, at least one alkyl group, at least one hydroxyl group; at least one alkoxy group, at least one hydroxyalkyl group or at least one amino group or (di)alkylamino group; $R_4$ is hydrogen or $C_1-C_4$alkyl;

$X_1$ and $X_2$, independently from each other are selected from saturated or unsaturated $C_1-C_{30}$hydrocarbon chains, optionally interrupted by at least one bivalent group chosen from —N($R_1$)—; $N^+(R_1)(R_2)$—; —O—; —S—; —CO—; —$SO_2$—; and/or optionally interrupted by an optionally substituted, saturated or unsaturated, fused or non-fused, aromatic or nonaromatic (hetero)cyclic radical optionally comprising at least one identical or different heteroatom;

V is $C_1-C_3$alkylene, optionally substituted by hydroxy;

D is a radical chosen from —N(CO)—$R_3$;

$C_{sat}$ and $C'_{sat}$ independently from each other are optionally substituted, optionally cyclic, linear or branched $C_1-C_{18}$alkylene chains;

$R_1$ and $R_2$, independently from each other are chosen from hydrogen; $C_1-C_4$alkyl; hydroxyalkyl; or aminoalkyl;

$R_3$ is $C_1-C_4$alkyl; and p, q and r independently from each other are 0 or 1.

2. Compounds according to claim 1, wherein A is chosen from the radicals

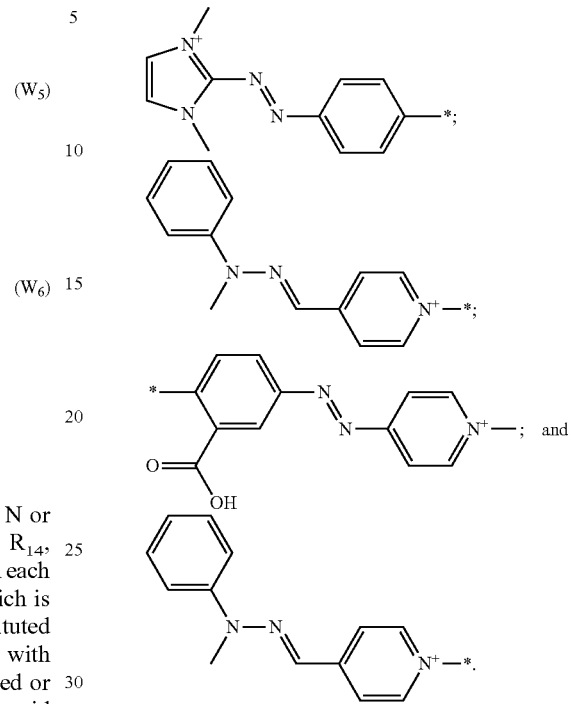

3. Compounds according to claim 1, wherein in formula (1) A is a radical of formula (1a) W—N═N—Ar—; or (1c) Ar—N($R_4$)—N═CH—W—;
V is —$(CH_2)_2$—;
p is 1; and
q is 0
wherein W and Ar are defined in claim 1.

4. Compounds according to claim 1, wherein in formula (2) A is a radical of formula (1a) W—N═N—Ar—; or (1c) Ar—N($R_4$)—N═CH—W—;
V is —$(CH_2)_2$—;
p is 1; and
q is 0
wherein W and Ar are defined in claim 1.

5. Compounds according to claim 1 corresponding to the compounds of formula

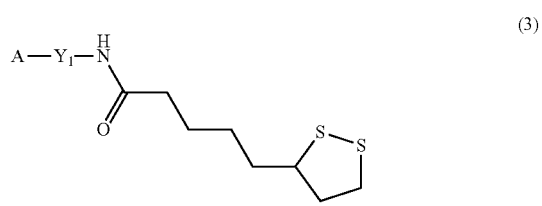
(3)

wherein
A is a radical of formula (1a) W—N═N—Ar—; or (1b) Ar—N═N—W—; and
$Y_1$ is a biradical selected from phenylene; cyclohexylene; and $C_1-C_3$alkylene; and
W is defined in claim 1; and
Ar is defined as $C_5$ or $C_6$aryl radicals and aromatic bicycles of the naphthyl type, which are optionally substituted with at least one halogen atom, at least one alkyl group, at least one hydroxyl group; at least one alkoxy group, at least one hydroxyalkyl group or at least one amino group or (di)alkylamino group.

6. Compounds according to claim 1 corresponding to the compounds of formula

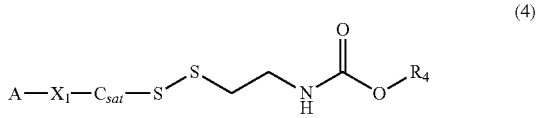

(4)

wherein
A is a radical of formula (1a) W—N=N—Ar—; or (1b) Ar—N=N—W—;
$R_4$ is methyl; or tert. butyl; and
W is defined in claim 1;
$X_1$, $C_{sat}$ are defined as in claim 1; and
Ar is defined as $C_5$ or $C_6$aryl radicals and aromatic bicycles of the naphthyl type, which are optionally substituted with at least one halogen atom, at least one alkyl group, at least one hydroxyl group; at least one alkoxy group, at least one hydroxyalkyl group or at least one amino group or (di)alkylamino group.

7. Compounds according to claim 5, wherein
A is a radical of formula

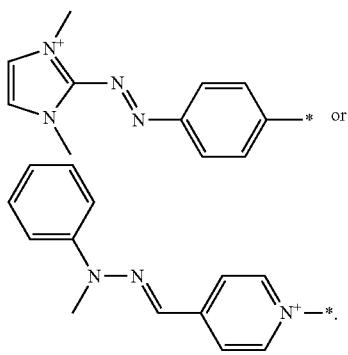

8. A method for dyeing human keratin fibers comprising applying to the fibers a dyeing composition comprising, in an appropriate cosmetic medium, at least one disulphide dye chosen from the dyes of the formulas (1) or (2) according to claim 1.

9. A method according to claim 8, wherein the dyeing composition further comprises at least one reducing agent.

10. A method according to claim 8, comprising pre-treating the keratin fibers with at least one reducing agent before applying the dyeing composition.

11. A method according to claim 8, comprising treating the keratin fibers with at least one reducing agent after applying the dyeing composition (post-treatment).

12. A method according to claim 11, wherein the at least one reducing agent is chosen from thiols, phosphines, bisulphite and sulphites.

13. A method according to claim 12, wherein the at least one reducing agent is chosen from thioglycolic acid, cysteine, homocysteine, thiolactic acid and the salts of these thiols.

14. A method according to claim 13, wherein the at least one reducing agent is chosen from thiols, phosphines, bisulphite and sulphites.

15. A method according to claim 14, wherein the at least one reducing agent is chosen from thioglycolic acid, cysteine, homocysteine, thiolactic acid and the salts of these thiols.

16. A method according to claim 8, wherein the dyeing composition further comprises at least one oxidizing agent.

17. A method according to claim 8, comprising post-treating the keratin fibers with at least one oxidizing agent.

18. A method according to claim 8, comprising post-treating the keratin fibers with at least one conditioning agent and optionally also post-treating the keratin fibers with at least one oxidizing agent.

19. A method according to claim 18, in which the oxidizing agent is chosen from hydrogen peroxide, urea peroxide, alkali metal bromates, persalts, and enzymes.

20. A method according to claim 8, wherein the at least one disulphide dye of formula (1) or (2) is present in the dyeing composition in an amount ranging from 0.001 to 50% by weight, relative to the total weight of the composition.

21. A dyeing composition comprising, in an appropriate cosmetic medium, at least one disulphide dye chosen from the dyes of the formula (1) and (2) according to claim 1.

* * * * *